(12) United States Patent
Iyer et al.

(10) Patent No.: US 8,706,228 B2
(45) Date of Patent: *Apr. 22, 2014

(54) ELECTRONIC MODULE ASSEMBLY FOR FILTERED FEEDTHROUGHS

(75) Inventors: Rajesh V. Iyer, Eden Prairie, MN (US);
Lea A. Nygren, Bloomington, MN (US);
Stephanie L. McCracken, Minneapolis, MN (US); Mukul Jain, Woodbury, MN (US); Steven M Dufon, Ramsey, MN (US); Christine Gale Kronich, Saint Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 705 days.

This patent is subject to a terminal disclaimer.

(21) Appl. No.: 12/750,687

(22) Filed: Mar. 30, 2010

(65) Prior Publication Data

US 2010/0256695 A1   Oct. 7, 2010

Related U.S. Application Data

(60) Provisional application No. 61/165,327, filed on Mar. 31, 2009.

(51) Int. Cl.
*A61N 1/00* (2006.01)
(52) U.S. Cl.
USPC ............................................................ 607/36
(58) Field of Classification Search
None
See application file for complete search history.

(56) References Cited

U.S. PATENT DOCUMENTS

| 5,905,627 | A | 5/1999 | Brendel et al. |
| 6,768,629 | B1 | 7/2004 | Allen et al. |
| 2003/0069612 | A1 | 4/2003 | Zart et al. |
| 2007/0043399 | A1 | 2/2007 | Stevenson et al. |
| 2007/0179551 | A1 | 8/2007 | Iyer et al. |
| 2007/0179554 | A1 | 8/2007 | Iyer et al. |

FOREIGN PATENT DOCUMENTS

| WO | WO 2007/087487 | 8/2007 |
| WO | WO 2008/103166 | 8/2008 |

OTHER PUBLICATIONS (PCT/US2010/029340) PCT Notification of Transmittal of the International Search Report and the Written Opinion of the International Searching Authority, Jul. 12, 2010.
(PCT/US2010/029345) PCT Notification of Transmittal of the International Search Report and the Written Opinion of the International Searching Authority, Aug. 24, 2010.

*Primary Examiner* — Christopher D Koharski
*Assistant Examiner* — Elizabeth K So
(74) *Attorney, Agent, or Firm* — Carol F. Barry

(57) ABSTRACT

An electronic module assembly (EMA) for an implantable medical device is disclosed. The EMA includes conductive strips connected to a non-conductive block. The non-conductive block possesses, a top side, a bottom side, a front side and a back side. A seamless non-conductive barrier extends from the bottom side and between the front side and the back side. The barrier prevents a pin from contacting another pin and eliminates welding of the ground pin to the side of the ferrule.

12 Claims, 20 Drawing Sheets

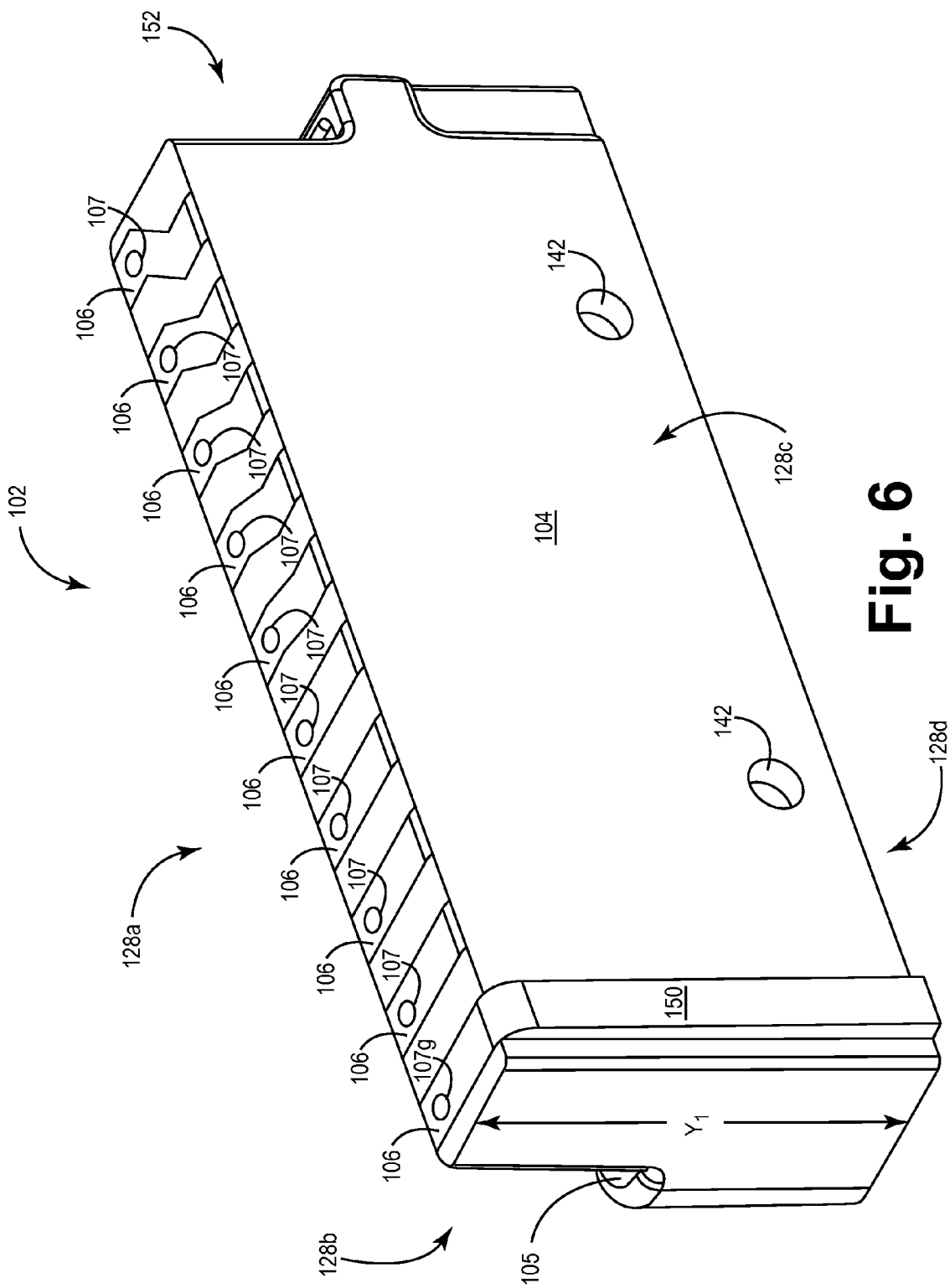

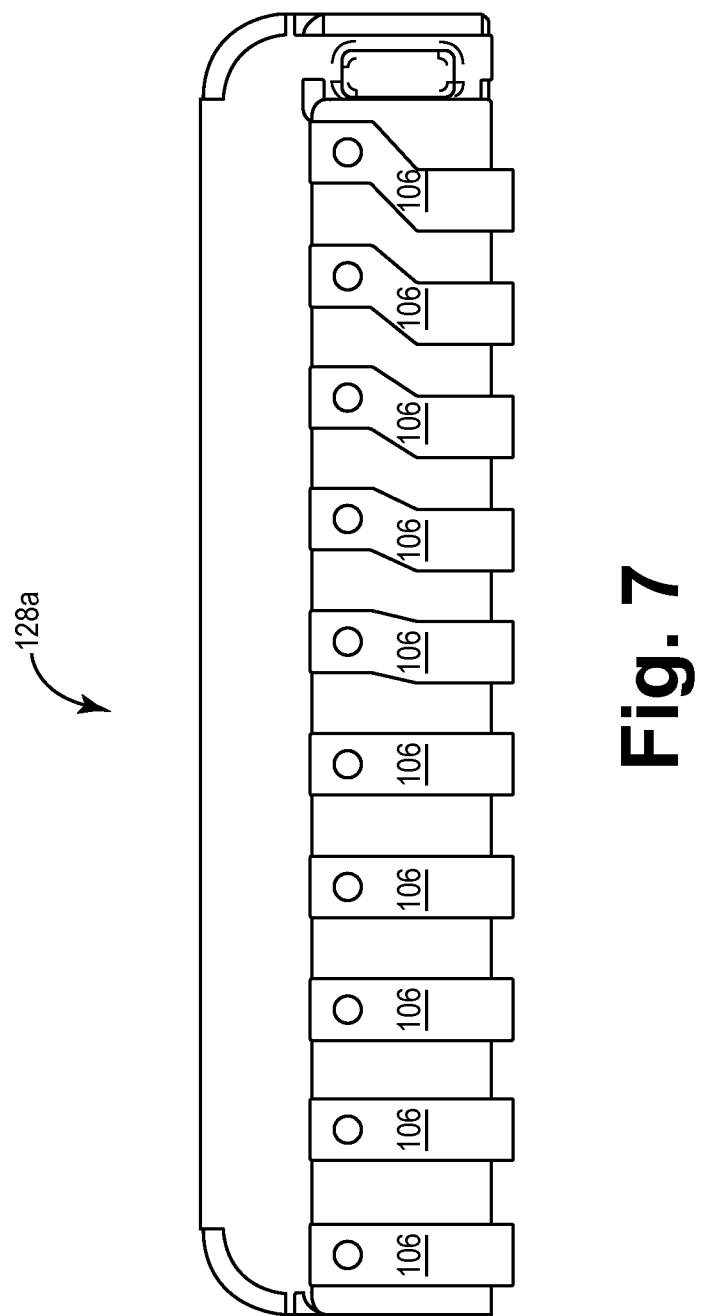

ELECTRONIC MODULE ASSEMBLY FOR FILTERED FEEDTHROUGHS

CROSS-REFERENCE TO RELATED APPLICATIONS

This application claims the benefit of U.S. Provisional Application No. 61/165,327, filed on Mar. 31, 2009. The disclosure of the above application is incorporated herein by reference.

TECHNICAL FIELD

The present disclosure relates generally to implantable medical devices, and, more particularly, to a filtered feedthrough electronic module assembly.

BACKGROUND

Implantable medical devices (IMDs) typically include a housing that encloses a variety of internal components, and protects the components from an implanted environment. For example, within the human body, the housing is sealed to prevent introduction of fluids or moisture to the internal components of an implantable medical device (IMD). In many cases, the IMD includes external components that extend outside of the housing and communicate with the internal components.

One example is an implantable cardioverter/defibrillator (ICD), which includes an internal battery, at least one charging capacitor, and electronic circuitry. The electronic circuitry typically is coupled to pacing and/or diagnostic leads that extend outside of the device housing for positioning within or near the targeted tissue such as the heart. To protect internal components while permitting electrical connections with external components, the ICD includes a connector body coupled to a filtered feedthrough electronic module assembly (FFEMA). FFEMA ensures that a seal exists between the electronic components inside and outside of the implantable medical device. FFEMA comprises an electronic module assembly (EMA) and a feedthrough assembly. The feedthrough pins, which extend from the feedthrough assembly, are laser welded to conductive strips on the EMA. A further processing step includes welding at least one of the feedthrough pins to a ferrule, which forms the ground connection, for the feedthrough assembly.

Yet another manufacturing processing operation involves adhering the ferrule to the EMA through epoxy. Moreover, an operator will occasionally incorrectly connect the EMA to the feedthrough assembly before applying the epoxy between the EMA and the ferrule. Incorrect assembly of the feedthrough assembly and the EMA can sometimes result in the EMA and/or feedthrough assembly being discarded.

Efforts to simplify or reduce the complexity, cost, and time of the manufacturing and assembly process can directly impact the cost of the implantable medical device for patients. Accordingly, more simple and cost-effective device assembly processes for implantable medical devices are desirable.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 6 is a schematic view of an electronic module block that includes a barrier to isolate the ground pin from the other feedthrough pins;

FIG. 7 is a schematic top view of an electronic module block of FIG. 6;

DETAILED DESCRIPTION

The following description is merely exemplary in nature and is not intended to limit the present disclosure, application, or uses. The devices described herein include an exemplary number of leads, etc. One will understand that the components, including number and kind, may be varied without altering the scope of the disclosure. Also, devices according to various embodiments may be used in any appropriate diagnostic or treatment procedure, including a cardiac procedure.

An implantable medical device (IMD) is disclosed. The IMD includes a housing, a connector body, and a filtered feedthrough electronic module assembly (FFEMA). The housing is connected to the connector body and the FFEMA. The FFEMA comprises a filtered feedthrough assembly connected to an electronic module assembly (EMA). The EMA includes conductive strips connected to either a top side, a bottom side, a front side or a back side of a non-conductive block. In one or more embodiments, a seamless non-conductive barrier extends from the bottom side and between the front side and the back side of the non-conductive block. The barrier prevents a pin from contacting another pin and eliminates welding of the ground pin to the side of the ferrule.

In one or more embodiments, the EMA's non-conductive block can include protruding members in order to form a "snap-fit" to the apertures located in the ferrule of the feedthrough assembly.

Figure 1:
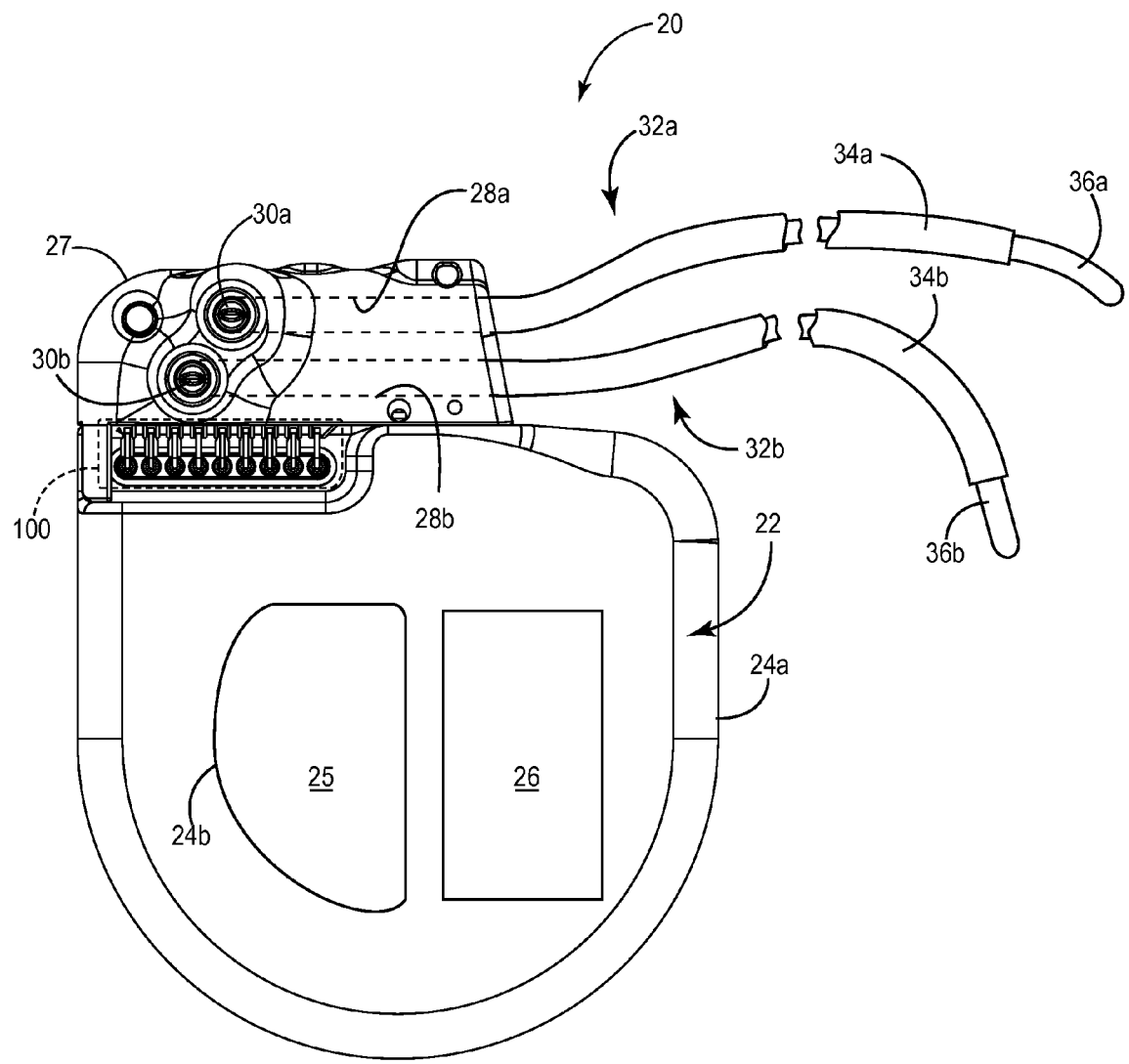
FIG. 1 is a conceptual schematic angled view of an implantable medical device (IMD) in which medical electrical leads extend therefrom.
Figure 2:
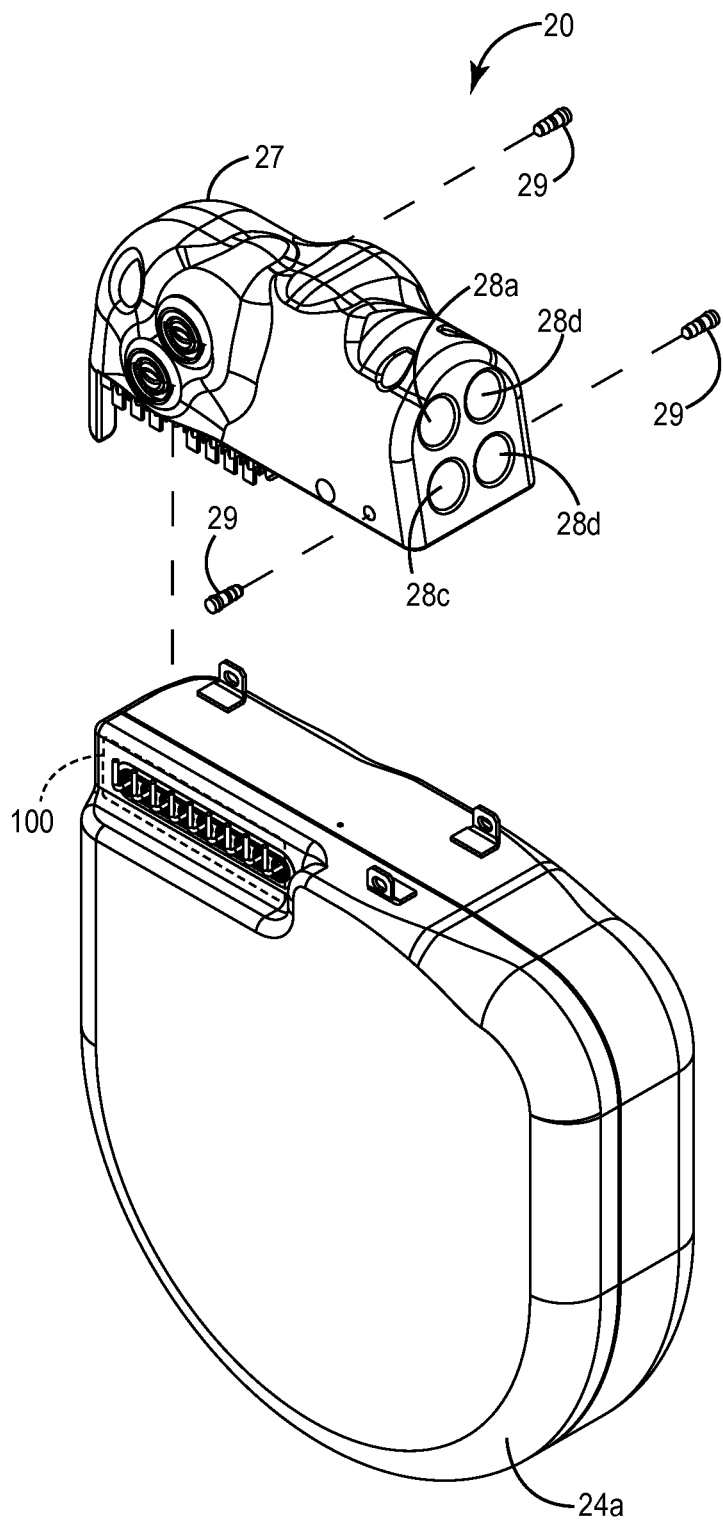
FIG. 2 is a schematic top view of the IMD depicted in FIG. 1 without leads being shown.

With reference to FIG. 1, an implantable medical device (IMD) 20 can include implantable pacemakers, implantable cardioverter defibrillator (ICD) devices, cardiac resynchronization therapy defibrillator devices, neurostimulators, drug pumps or combinations thereof. Exemplary IMDs are commercially available as including one generally known to those skilled in the art, such as the Medtronic CONCERTO™, SENSIA™, VIRTUOSO™, RESTORE™, RESTORE ULTRA™, sold by Medtronic, Inc. of Minnesota. IMD 20 can include an implantable case, housing or body assembly 22. Implantable case 22 can be formed of appropriate materials and include appropriate features, such as a hermetically sealed body wall 24a. Body wall 24a comprises substantially conductive material such as titanium.

Contained within or associated with case 22 can be a power device 25 such as one or more batteries and/or capacitors encased in housing or case body wall 24b, a controller assembly 26, and a connector body 27. Controller assembly 26 can include a circuit board having a processor, memory, transmitter, receiver, and/or other appropriate portions. Connector body 27 can extend from or be integrated with case 22. At its distal end, connector body 27 can include one or more ports 28a,b that interconnects with one or more connector terminals 30a,b of one or more lead assemblies 32a,b. Exemplary connector bodies 27 can include IS-1 connectors, IS-4 connectors or other suitable connectors. Lead assemblies 32a,b generally include respective lead bodies 34a,b each having a respective tip electrode 36a,b. For example, the first lead assembly 32a can include an active tip electrode 36a and the second lead assembly can include a passive tip electrode 36b.

At its distal end, connector body 27 is connected via connectors or set screws 29 to lead assemblies 32a,b. Set screws 29 force lead assemblies 32a,b in place to form an electrical connection via connector body 27, which, at its proximal end, is connected to a filtered feedthrough electronic module assembly (FFEMA) 100, as depicted in FIGS. 3A-5B. FFEMA 100 electrically connects circuitry inside a sealed case of the IMD to a connector body 27, which connects with external components that extend outside of the housing. FFEMA 100 comprises an electronic module assembly (EMA) 102 connected to a feedthrough assembly 120. The EMA 102 is composed of a non-conductive block, referred to as an electronic module block (EMB) 104, with a set of conductive strips 106 or conductive elements connected to the EMB.

EMB 104 includes a top side 128a, a bottom side 128d, a front side 128b, a back side 128c, and shortened ends 152. Top side 128a, shown in FIG. 7, possesses a flat or substantially flat surface. A number of openings or apertures 109 are defined through the body 102 between top and bottom sides 128a,d, respectively. The openings 109 are capable of accepting or receiving feedthrough pins 107 or conductors. EMB 104 is formed of, for example, silicone, polyurethane and/or other suitable material.

Figure 8:
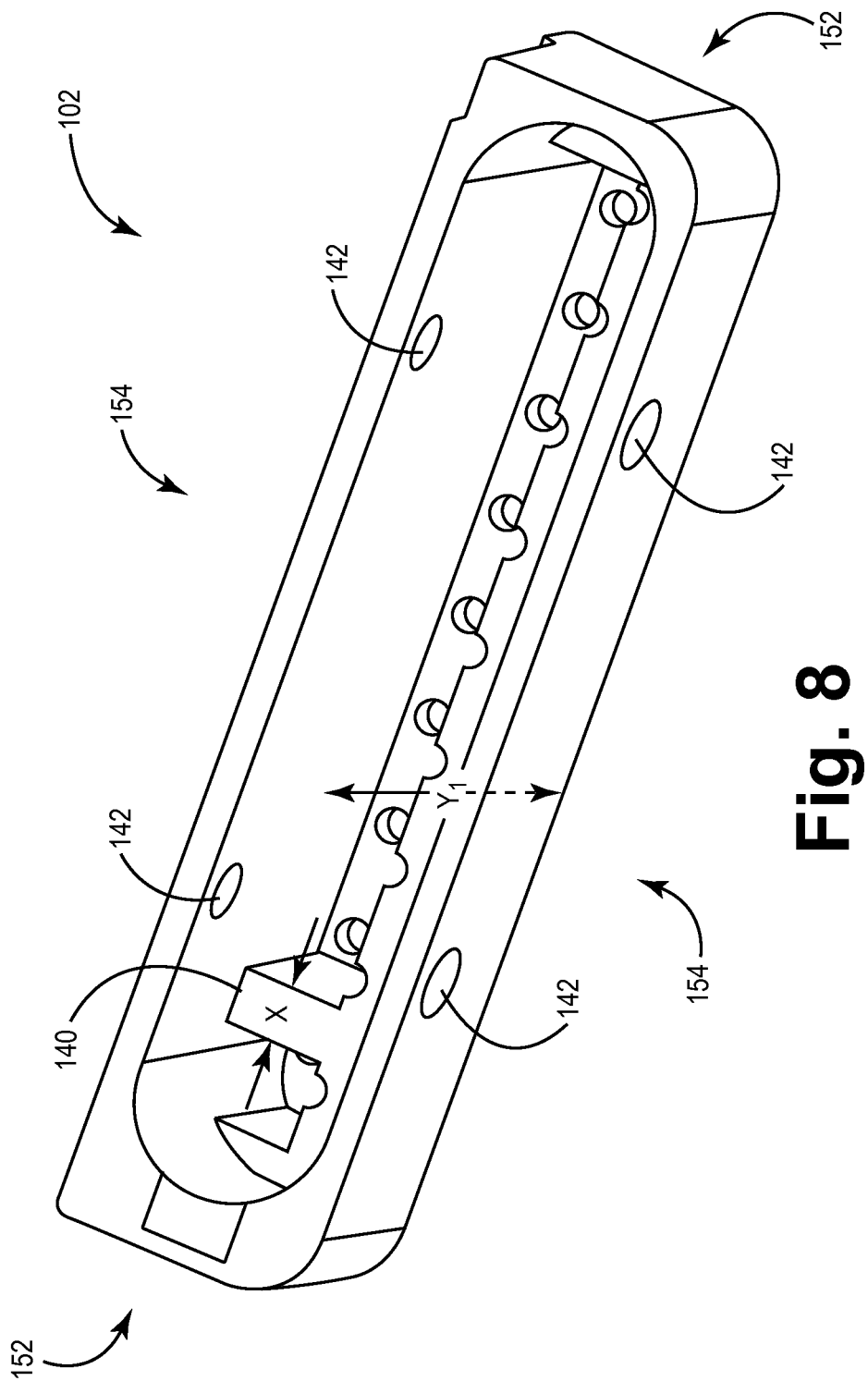
FIG. 8 is a schematic bottom view of an electronic module block of FIG. 6.
Figure 9:
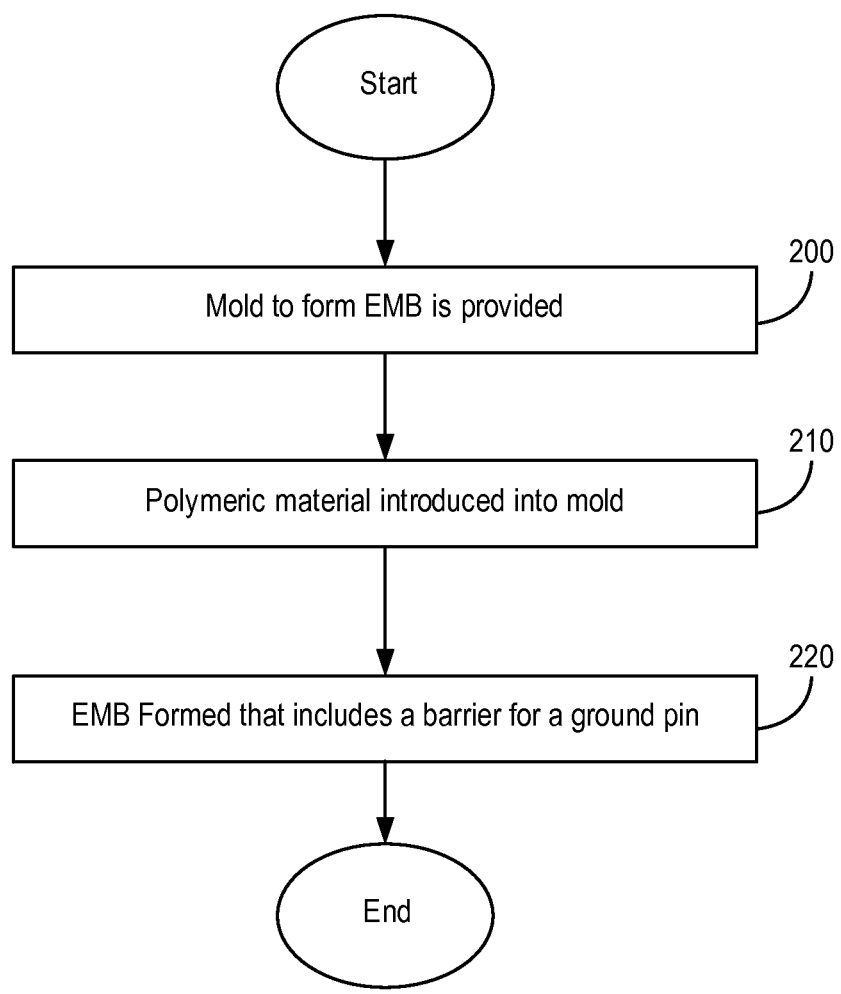
FIG. 9 depicts a flow diagram for forming an EMA with an insulating barrier for a ground pin.

Referring to FIGS. 6, and 8, EMB 104 includes a non-conductive or insulative barrier 140 that forms a portion of a substantially cylindrical case 150 for housing or receiving a ground pin 107g, which prevents ground pin 107g from contacting the remaining feedthrough pins 107. Barrier 140 is integrally and/or seamlessly formed as part of EMB 104. Barrier 140 is located directly adjacent to, or, at an interior end to one of the shortened ends 152 of EMB 104. Barrier 140 possesses a thickness, designated as X. Barrier 140 can comprise the same material as EMB 104 or other suitable polymeric material used, for example, in a two-shot molding process. By including barrier 140 in EMB 104, manufacturing processes are simplified, efficient and costs are reduced to create an IMD for a patient. For example, barrier 140 creates a self-alignment feature for ground pin 107g. Additionally, barrier 140 eliminates formation of a separate insulative sheath that is separately applied to the ground pin 107g.

Figure 4A:
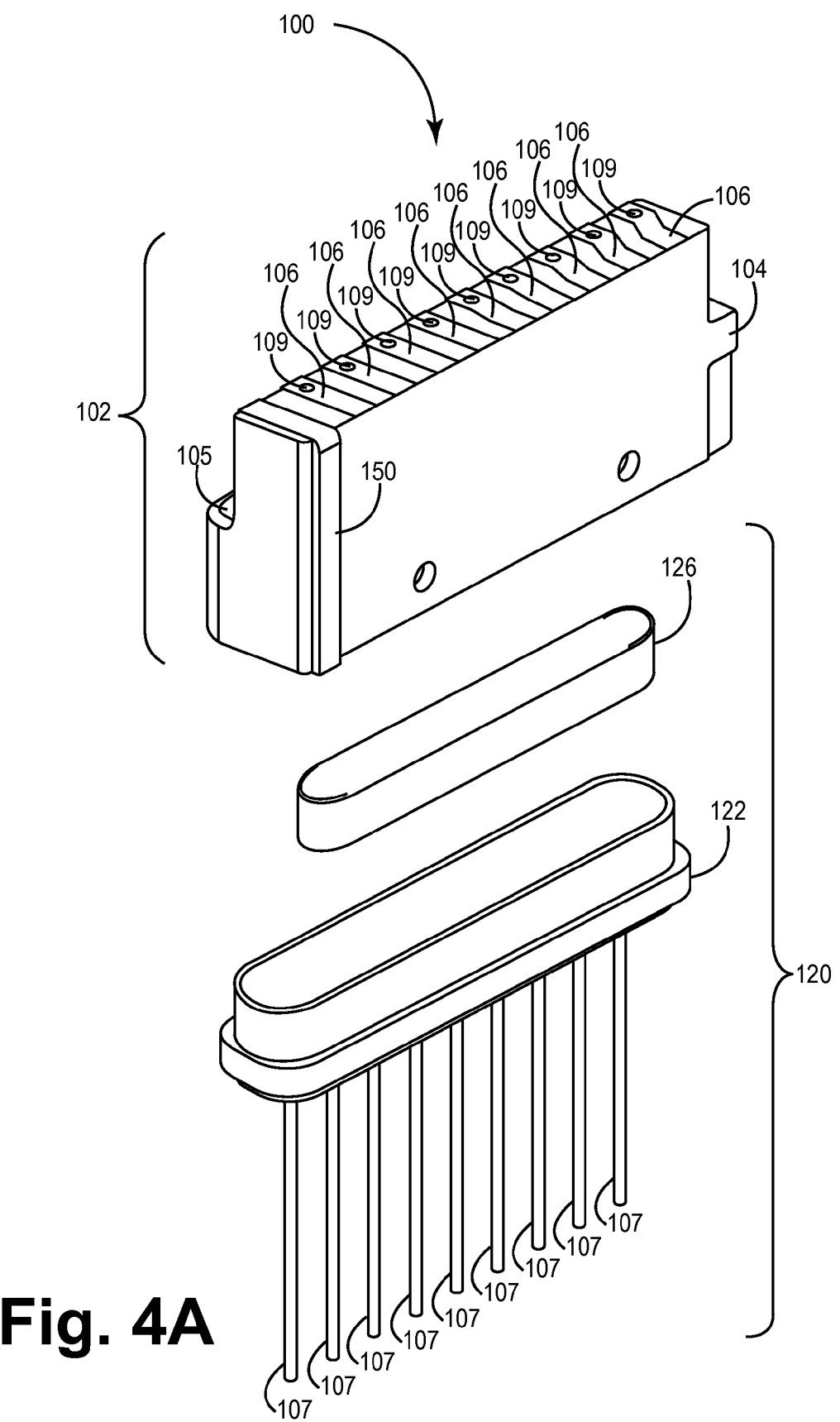
FIG. 4A is a schematic view of components used to form a FFEMA for the IMD depicted in FIGS. 3A-3B.
Figure 4B:
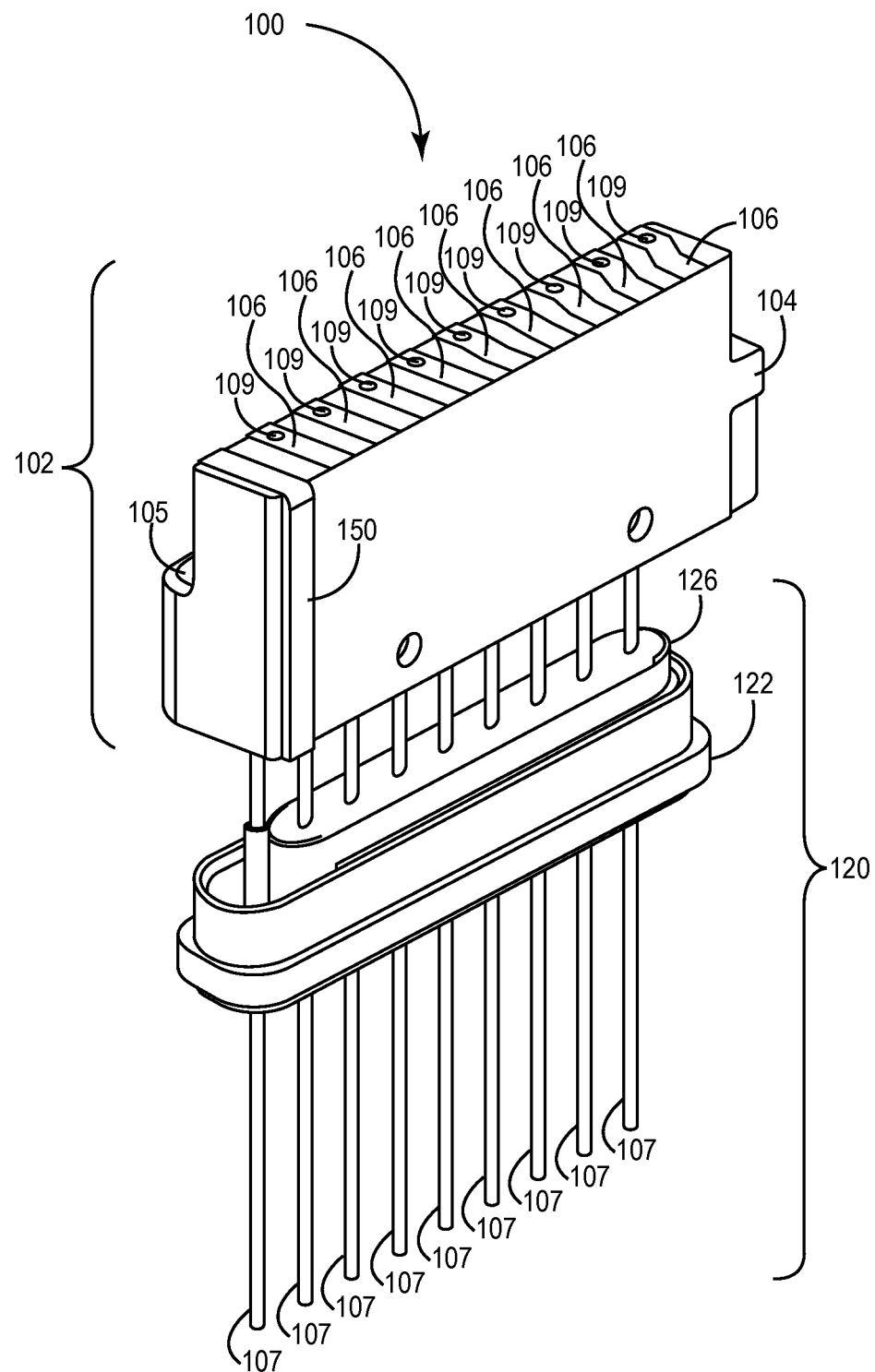
FIG. 4B is a schematic view of a partially assembled FFEMA for the IMD depicted in FIGS. 3A-3B.
Figure 5A:
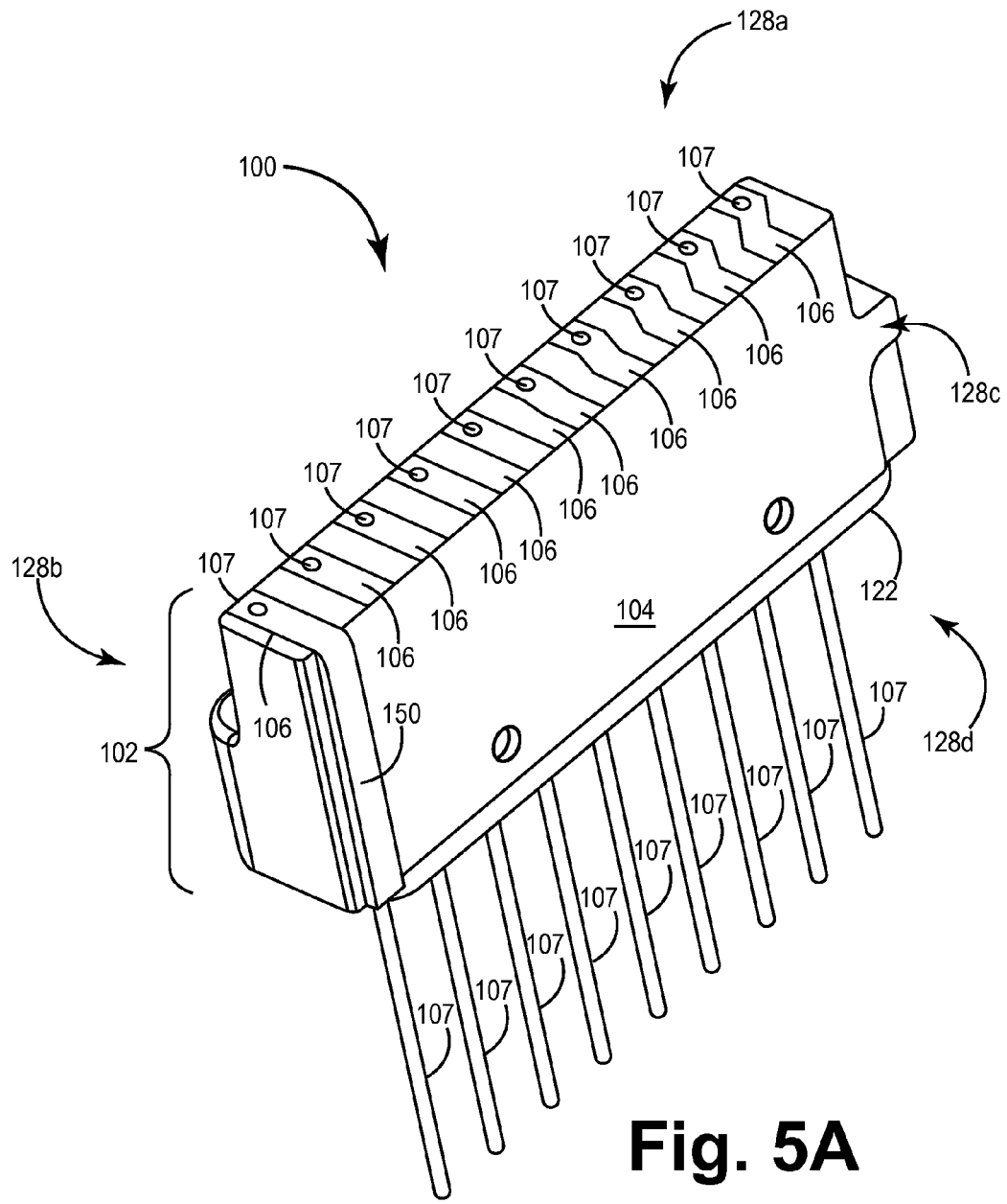
FIG. 5A is a schematic view of a FFEMA for the IMD depicted in FIGS. 3A-3B.
Figure 5B:
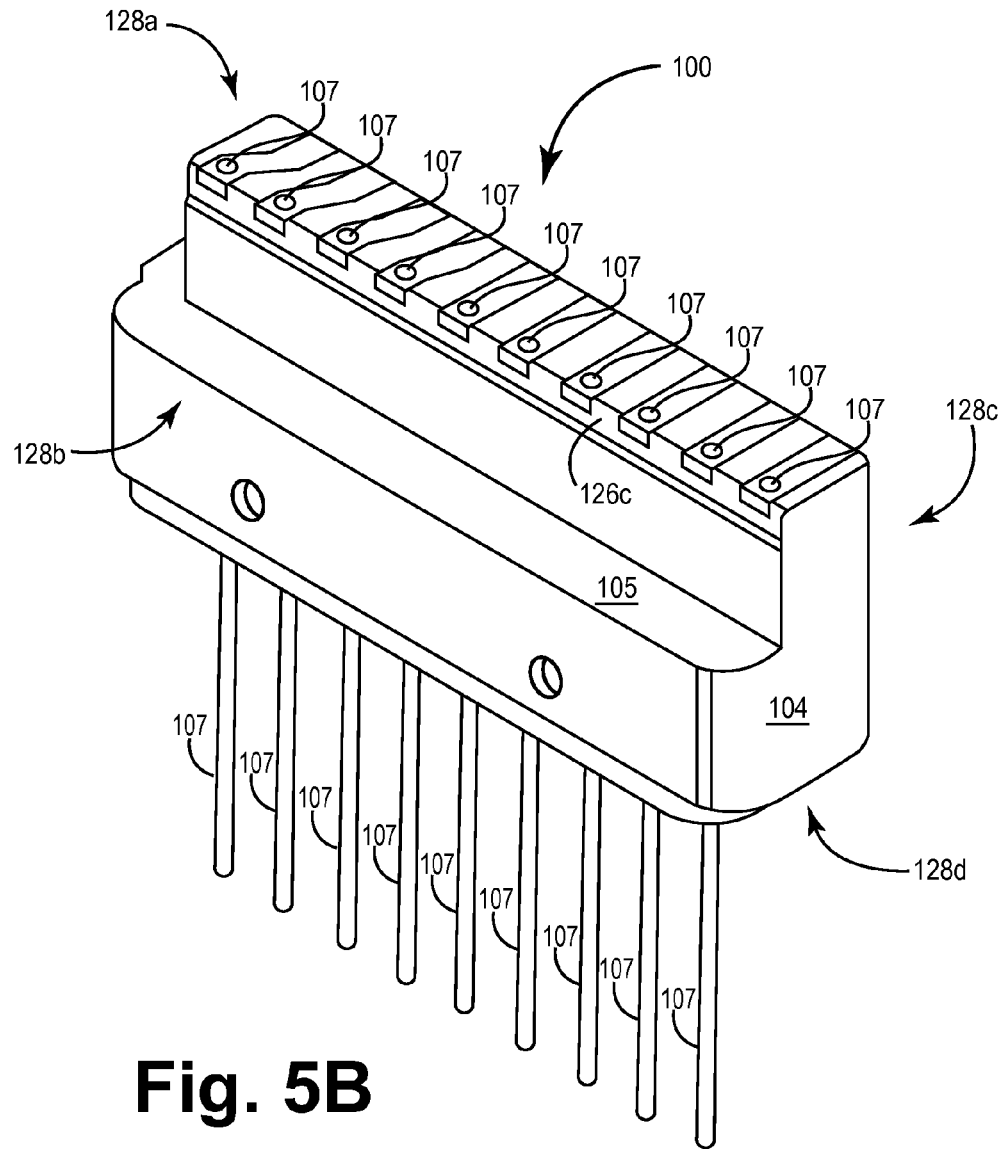
FIG. 5B is a schematic view of a FFEMA for the IMD depicted in FIGS. 3A-3B.

After EMB 104 is formed with barrier 140, EMA 102 and feedthrough assembly 120 are conventionally formed. For example, a set of conductive strips 106 are electrically and mechanically coupled to the EMB 104, which forms EMA 102. Feedthrough assembly 120, depicted in FIGS. 4A-B, is conventionally formed and connected to EMA 102 in order to create FFEMA 100. Each multipolar feedthrough element 120 includes a feedthrough member, conductor or pin 107, a ferrule 122, a capacitive element 126, an insulator member or element (not shown), and conductive material (not shown) (also referred to as a conductive element). An exemplary multipolar feedthrough element that shows the configuration of the insulator member and conductive material around the pin may be seen with respect to U.S. patent application Ser. No. 12/183,593, filed Jul. 31, 2008 entitled "NOVEL CAPACITIVE ELEMENTS AND FILTERED FEEDTHROUGH ASSEMBLIES FOR IMPLANTABLE MEDICAL DEVICES", and assigned to the assignee of the present invention, the disclosure of which is incorporated by reference in its entirety herein.

Suitable materials for feedthrough members 107 and ferrule 122 can include titanium, niobium, platinum, platinum/iridium, molybdenum, zirconium, tantalum or alloys thereof. The insulator element can comprise an insulative material such as glass, ceramic or other suitable materials. The conductive material can be a conductive epoxy, a conductive polyimide, a conductive solder or other suitable materials. An exemplary conductive epoxy can be Ablebond 8700E commercially available from Ablestik Inc., located in Rancho Dominguez, Calif.; an exemplary conductive polyimide can include Ablebond 71-1 from Ablestik Inc., and exemplary conductive solders can be indium-based, tin-based, gold-based solder, and/or lead based.

Figure 3A:
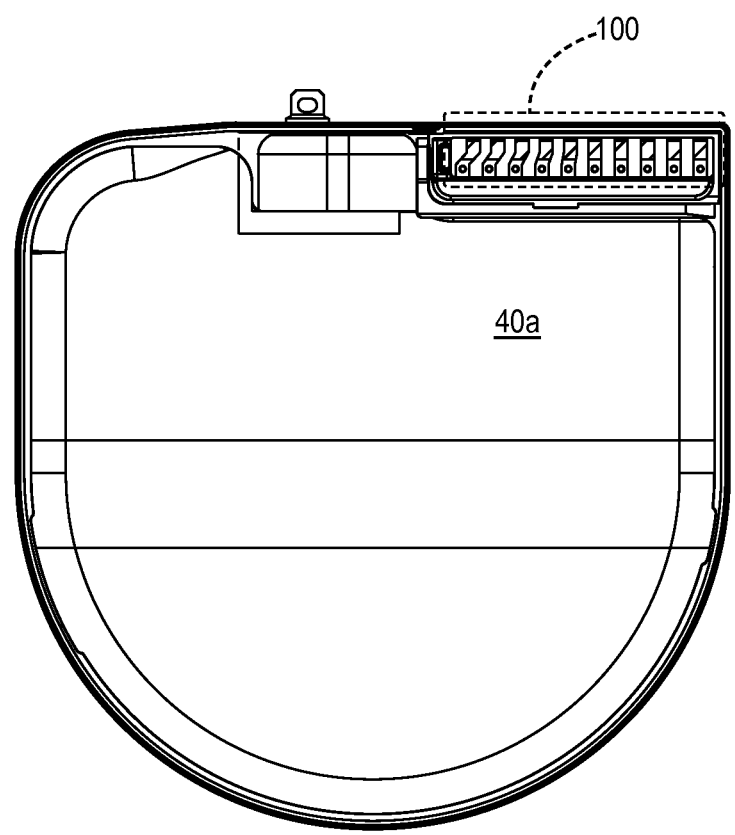
FIG. 3A is a schematic interior view of one side of a housing to an IMD that includes a top side view of a filtered feedthrough electronic module assembly (FFEMA)
Figure 3B:
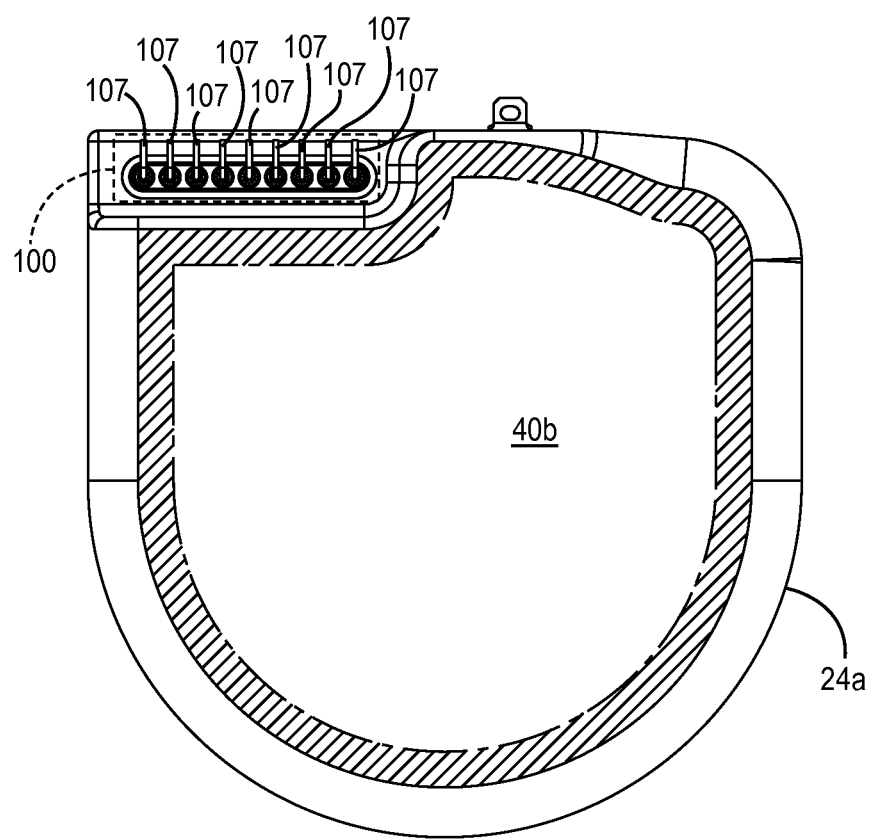
FIG. 3B is a schematic exterior view of the other side of a housing depicted in FIG. 3A to an IMD along with a back side view of a FFEMA.
Figure 3C:
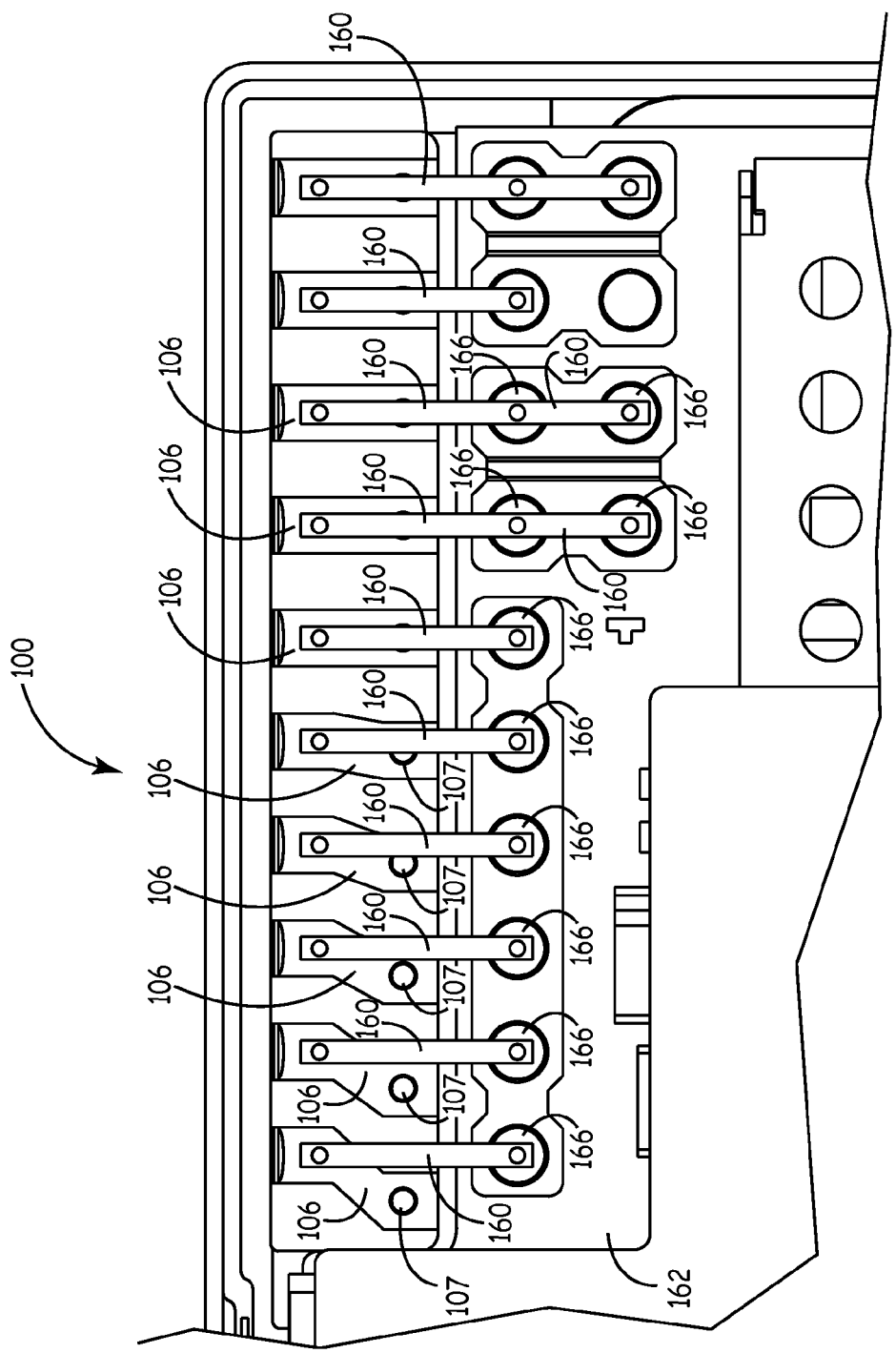
FIG. 3C is a schematic cutaway view of the FFEMA depicted in FIGS. 3A-3B.

The electrically grounded ferrule 122 holds or supports an array of feedthrough pins 107 extending through the ferrule 122. A monolithic discoidal capacitor assembly 126 is positioned around at least some of the feedthrough pins 107. The capacitor assembly 126 is held together by a monolithic body. The capacitor assembly 126 is electrically connected between a feedthrough pin 107 and ground such as to the ferrule 122 to provide low-pass electromagnetic interference (EMI) filtering. EMA 104 can be positioned over the feedthrough pins 107 and the discoidal capacitor assembly 126, as shown in FIG. 4A. Feedthrough pins 107 pass through holes or apertures 109 and contact the conductive strips 106 on the EMA 102. Feedthrough pins 107 are then trimmed flush to the conductive strips 106 and laser welded such that the trimmed pins make an electrical connection to the conductive strips 106. Thereafter, as shown in FIG. 3C, a conductive ribbon 160 or weld connects one or more feedthrough pins 107 to one or more corresponding bond pads 166 on a hybrid assembly or circuit board 162.

FIG. 8 depicts a method of forming an EMA 102. At block 200, a mold is provided that is configured to form a non-conductive block or EMB 102 with a top side, a bottom side, a front side, and a bottom side. The mold possesses features that provide a surficial mirror image of EMB 102. The first side of the mold forms the top side of the non-conductive block, the second side of the mold forms the back side of the non-conductive block, and the third side of the mold forms the front side of the mold. The front side is directly adjacent to the top side and the top side is directly adjacent to the back side of the non-conductive block. The mold also includes a recessed region that extends from the bottom side and between the front and back sides so that a barrier can be formed. In one or more embodiments, a polymer such as silicone, polyurethane and/or PEEK can be introduced or placed into the mold to form EMB 104. At block 210, a plurality of conductive strips are placed in the mold at one or more sides such as a first side, a second side and a third side of the mold. Each conductive strip is formed of titanium or nickel and plated and/or sputtered with gold and/or platinum to provide a low resistance path to the hybrid assembly. At block 220, a polymeric material is introduced or placed into the mold. At block 230, the EMA is formed such that the non-conductive block has a top side, a back side, a front side, and a bottom side.

Another set of embodiments are depicted relative to FIGS. 10-17. In one or more embodiments, EMB 104 includes one or more protruding members 170 or tabs, which can mate with holes or apertures in ferrule 122 in order to form a snap-fit mating configuration. A snap-fit mating configuration can produce a snapping or clicking sound once two objects are coupled together. Referring briefly to FIG. 16A, protruding member 170 is configured to easily form a snap-fit with ferrule 122. Referring to FIG. 16B, in one or more embodiments, protruding member 170 can be substantially trapezoidal in shape; however, other suitable shapes may also be used. In one or more embodiments, protruding member 170 extends from end 182 of EMB 104. Protruding member 170 can include a slanted surface 172, substantially straight surfaces 174, 175, along with two opposing exterior surfaces 178. Opposing surfaces 178 can be substantially straight or curved. Slanted surface 172 can possess a length of about 0.25 mm and can range from 0.1 mm to 1.5 mm. Slanted surface 172 can possess an angle θ relative to horizontal line 180. In one or more embodiments, angle θ is about 48 degrees (°). Substantially straight surface 175, in one or more embodiments, can possess a length of about 0.9 mm and can range from about 0.8 mm to about 2 mm. It is appreciated that a variety of other sizes or dimensions can be useful in forming protruding member 170.

Figure 10:
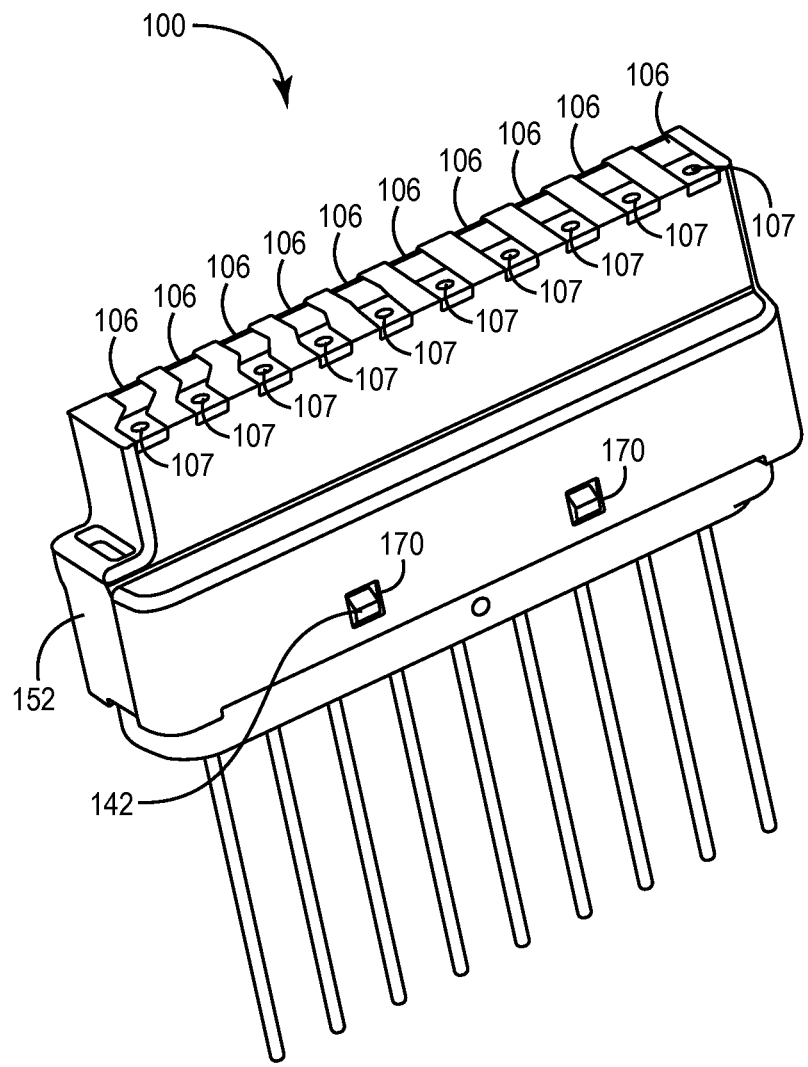
FIG. 10 is a schematic view of an electronic module block that includes at least one or more protruding members in order to form a "snap-fit" connection with a ferrule of a feedthrough assembly.
Figure 11:
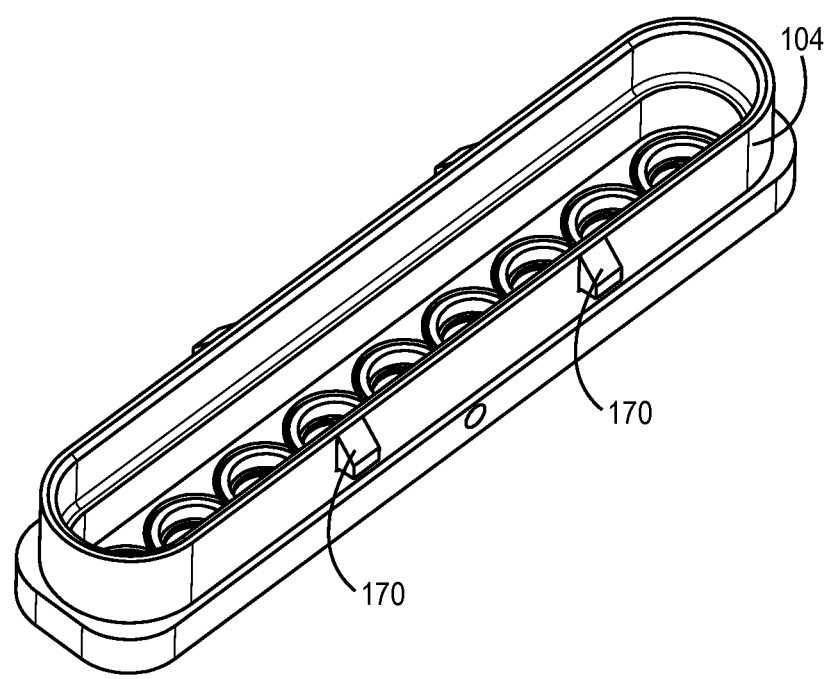
FIG. 11 is a schematic interior view of the electronic module block depicted in FIG. 10.
Figure 12:
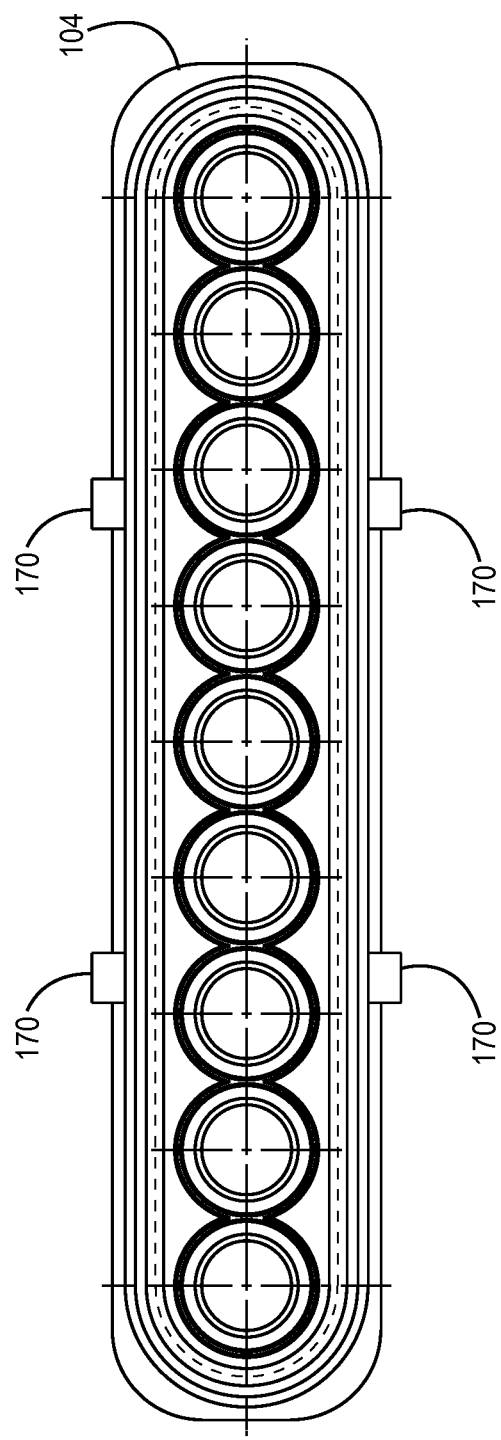
FIG. 12 is a schematic top interior view of the electronic module block depicted in FIG. 11.
Figure 13:
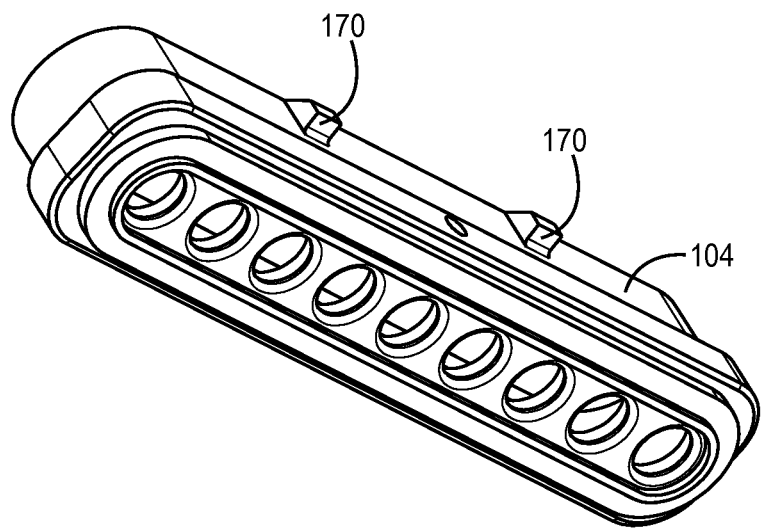
FIG. 13 is a schematic exterior view of the electronic module block depicted in FIG. 10.
Figure 14:
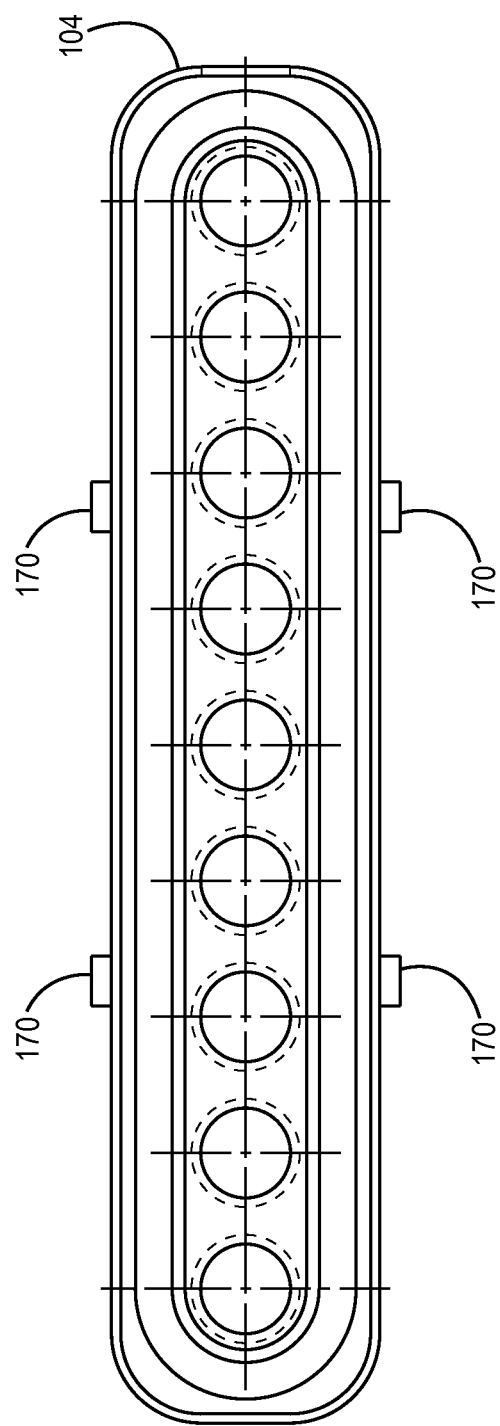
FIG. 14 is a schematic top exterior view of the electronic module block depicted in FIG. 13.
Figure 16A:
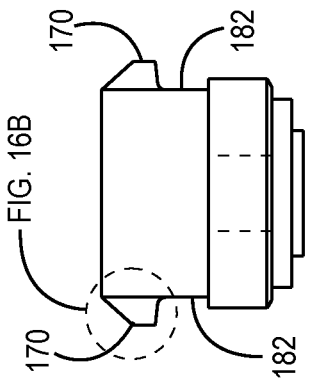
FIG. 16A is a schematic side view of the electronic module block from its shortened side with the protruding members extending outward.
Figure 15:
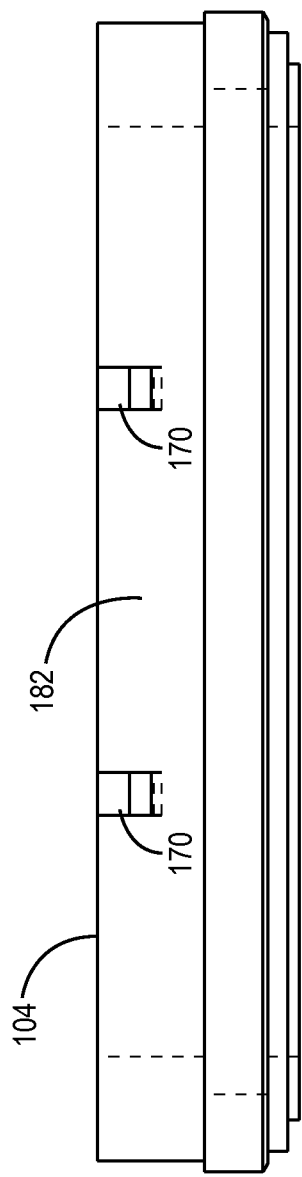
FIG. 15 is a schematic side view of the electronic module block from its elongated side with the protruding members extending outward.
Figure 16B:
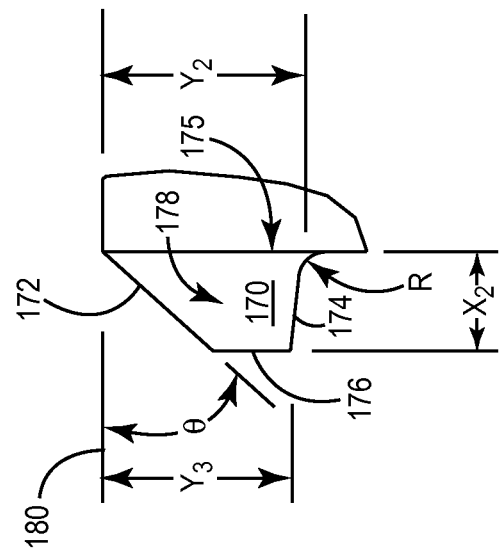
FIG. 16B is a schematic side view of a protruding member shown in FIG. 16A.

As shown in FIG. 10, protruding members 170 extend through apertures 142 of ferrule 122 to form a snap-fit mating configuration. In this embodiment, two protruding members 170 are depicted. However, it can be appreciated that one, two or more protruding members 170 can be implemented on back side 128c of EMB 104. Additionally, one or more protruding members 170 can be formed in the exterior of shortened ends 152. By forming a snap-fit mating configuration between EMB 104 and ferrule 122, the manufacturing process is simplified and the FFEMA 100 maybe improved. For example, a process that involves adhering EMB 104 to ferrule 122 is eliminated, which reduces time and materials used to form the present mating configuration between EMB 104 and ferrule 122.

Figure 17:
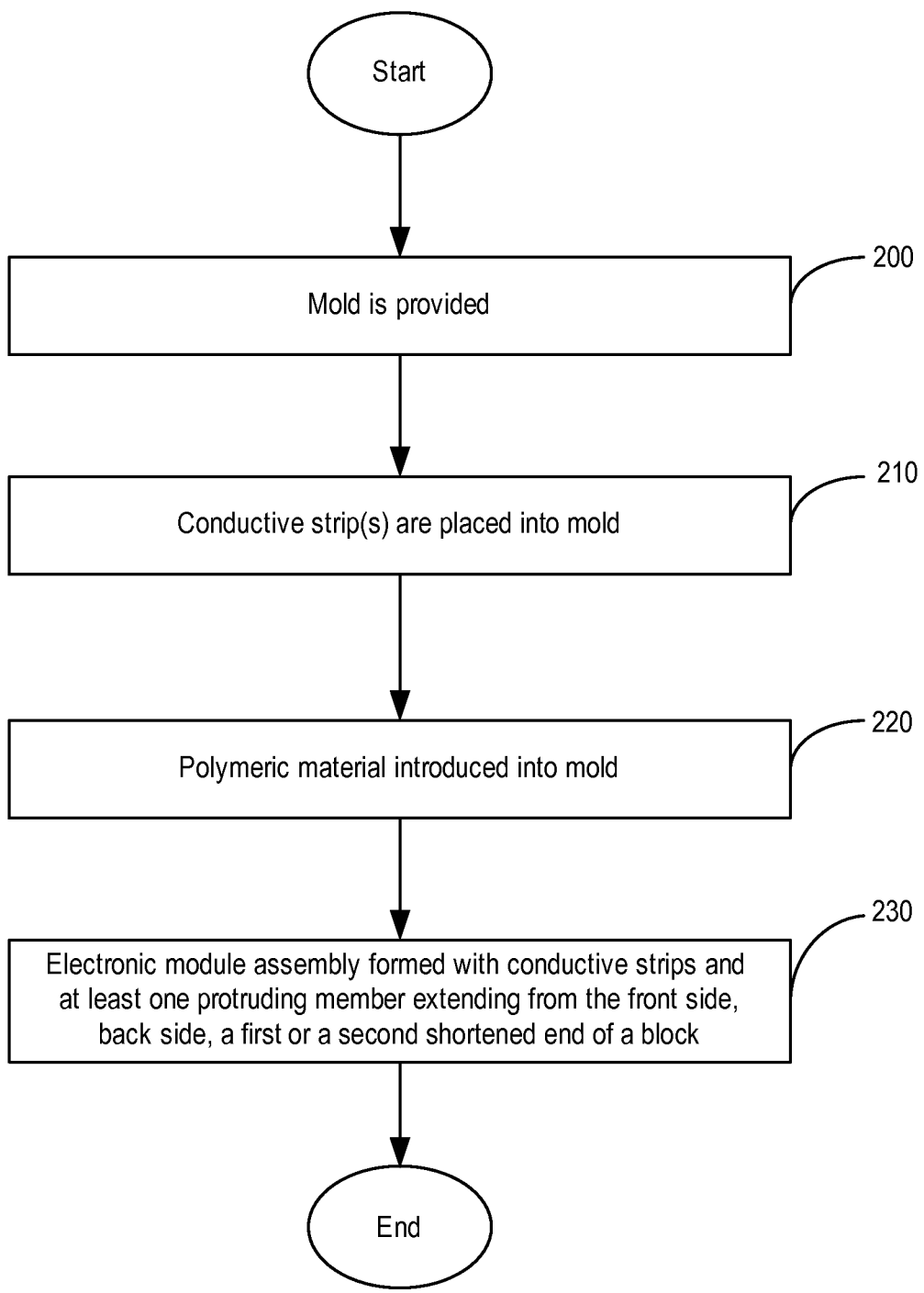
FIG. 17 depicts a flow diagram for forming an EMA with protruding members.

FIG. 17 depicts a method of forming an EMA 102. At block 200, a mold is provided that is configured to form a non-conductive block or EMB 102 with a top side, a bottom side, a front side, and a bottom side. The first side of the mold forms the top side of the non-conductive block, the second side of the mold forms the back side of the non-conductive block, and the third side of the mold forms the front side of the mold. The front side is directly adjacent to the top side and the top side is directly adjacent to the back side of the non-conductive block. In one or more other embodiments, the mold can further include "snap-fit" features to allow the EMA to snap into place relative to feedthrough assembly 120. For example, one or more protruding members is added to EMB 104. In one or more embodiments, a polymer such as silicone, polyurethane and/or PEEK can be introduced or placed into the mold to form EMB 104. At block 210, a plurality of conductive strips are placed in the mold at one or more sides such as a first side, a second side and a third side of the mold. Each conductive strip 106 is formed of titanium or nickel and plated and/or sputtered with gold/platinum to provide a low resistance path. At block 220, a polymeric material is introduced or placed into the mold. At block 230, the EMA is formed such that the non-conductive block has a top side, a back side, a front side, and a bottom side.

Although the present invention has been described in considerable detail with reference to certain disclosed embodiments, the disclosed embodiments are presented for purposes of illustration and not limitation and other embodiments of the invention are possible. It will be appreciated that various changes, adaptations, and modifications may be made without departing from the spirit of the invention and the scope of the appended claims.

What is claimed is:

1. An implantable medical device (IMD) comprising:
   a housing;
   a connector body coupled to the housing;
   a filtered feedthrough electronic module assembly (FFEMA) coupled to the connector body and to the housing, the FFEMA comprises:
   a filtered feedthrough assembly;
   an electronic module assembly (EMA) coupled to the filtered feedthrough assembly, the EMA comprises:
   a non-conductive block comprising a top side including a plurality of apertures, a bottom side, a front side, a back side, a first shortened end extending from the top side and between the front side and the back side, a second shortened end extending from the top side and between the front side and the back side, the second shortened end opposing the first shortened end, a cavity formed between the top side, bottom side, front side, back side, and the first and second shortened ends,
   a non-conductive barrier extending from the top side and between the front side and the back side, the barrier prevents a ground feedthrough pin from contacting another feedthrough pin; and
   a set of conductive strips coupled to the non-conductive block that correspond to a set of feedthrough pins that extend from the feedthrough assembly;
   wherein at least one feedthrough pin being coupled to a hybrid assembly.

2. The IMD of claim 1, wherein the barrier prevents the ground feedthrough pin from contacting a set of pins extending from the filtered feedthrough assembly.

3. The IMD of claim 2, wherein the barrier possesses a thickness of about 1 mm.

4. The IMD of claim 2, wherein the barrier possesses a height 2 mm to about 20 mm.

5. The IMD of claim 2, wherein the barrier possesses a diameter of 3 mm.

6. The IMD of claim 3, wherein the FFEMA is free of a weld contacting a ground pin to a side of a ferrule for the filtered feedthrough assembly.

7. An implantable medical device (IMD) comprising:
   a housing;
   a connector body coupled to the housing;
   a filtered feedthrough electronic module assembly (FFEMA) coupled to the connector body and to the housing, the FFEMA comprises:
      a filtered feedthrough assembly;
      an electronic module assembly (EMA) coupled to the filtered feedthrough assembly, the EMA comprises:
         a non-conductive block comprising a top side, a bottom side, a front side, a back side, a first shortened end extending from the top side and between the front side and the back side, a second shortened end extending from the top side and between the front side and the back side, the second shortened end opposing the first shortened end, a cavity formed between the top side, bottom side, front side, back side, and the first and second shortened ends,
         a non-conductive barrier extending across the cavity from the top side and between the front side and the back side, the barrier prevents a ground feedthrough pin from contacting another feedthrough pin, wherein the FFEMA is free of a weld connecting a ground pin to a side of a ferrule for the filtered feedthrough assembly; and
         a set of conductive strips coupled to the non-conductive block that correspond to a set of feedthrough pins that extend from the feedthrough assembly,
      wherein at least one feedthrough pin being coupled to a hybrid assembly.

8. The IMD of claim 7, wherein the barrier prevents the ground feedthrough pin from contacting a set of pins extending from the filtered feedthrough assembly.

9. The IMD of claim 7, wherein the barrier possesses a thickness of about 1 mm.

10. The IMD of claim 7, wherein the barrier possesses a height 2 mm to about 20 mm.

11. The IMD of claim 7, wherein the barrier possesses a diameter of 3 mm.

12. An implantable medical device (IMD) comprising:
   a housing;
   a connector body coupled to the housing;
   a filtered feedthrough electronic module assembly (FFEMA) coupled to the connector body and to the housing, the FFEMA comprises:
      a filtered feedthrough assembly;
      an electronic module assembly (EMA) coupled to the filtered feedthrough assembly, the EMA comprises:
         a non-conductive block comprising a top side, a bottom side, a front side, a back side, a first shortened end extending from the top side and between the front side and the back side, a second shortened end extending from the top side and between the front side and the back side, the second shortened end opposing the first shortened end, a cavity formed between the top side, bottom side, front side, back side, and the first and second shortened ends,
         a non-conductive barrier extending into the cavity from the top side and between the front side and the back side, the barrier prevents a ground feedthrough pin from contacting another feedthrough pin, wherein the FFEMA is free of a weld connecting a ground pin to a side of a ferrule for the filtered feedthrough assembly; and
         a set of conductive strips coupled to the non-conductive block that correspond to a set of feedthrough pins that extend from the feedthrough assembly,
      wherein at least one feedthrough pin being coupled to a hybrid assembly.

* * * * *